United States Patent
Hinman

(10) Patent No.: US 8,871,519 B2
(45) Date of Patent: Oct. 28, 2014

(54) METHOD OF QUALIFYING MATERIAL FOR USE IN CLEANING OF ALKYLENE OXIDE EQUIPMENT

(75) Inventor: Paul Victor Hinman, Charleston, WV (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 14/114,212

(22) PCT Filed: May 10, 2012

(86) PCT No.: PCT/US2012/037296
§ 371 (c)(1),
(2), (4) Date: Oct. 27, 2013

(87) PCT Pub. No.: WO2012/166312
PCT Pub. Date: Dec. 6, 2012

(65) Prior Publication Data
US 2014/0080219 A1    Mar. 20, 2014

Related U.S. Application Data

(60) Provisional application No. 61/490,722, filed on May 27, 2011.

(51) Int. Cl.
*G01N 33/00* (2006.01)
*C07D 301/10* (2006.01)
*B24C 1/08* (2006.01)

(52) U.S. Cl.
CPC ............ *G01N 33/0004* (2013.01); *B24C 1/086* (2013.01); *C07D 301/10* (2013.01)
USPC ............ 436/93; 436/127; 436/128; 436/133; 436/134; 436/142; 134/22.18; 549/523

(58) Field of Classification Search
USPC ................... 436/93, 127, 128, 133, 134, 142; 134/22.11, 22.12, 22.18; 549/523, 542
See application file for complete search history.

(56) References Cited

U.S. PATENT DOCUMENTS

| | | | |
|---|---|---|---|
| 2,883,346 A | 4/1959 | Alexander | |
| 4,391,735 A * | 7/1983 | Busse | 502/28 |
| 4,992,567 A | 2/1991 | Meyer | |
| 5,233,060 A * | 8/1993 | Pendergast et al. | 549/523 |
| 5,241,088 A | 8/1993 | Meyer | |
| 5,440,058 A | 8/1995 | Hoffman | |
| 6,514,908 B1 | 2/2003 | Kakimoto | |
| 8,513,444 B2 * | 8/2013 | Habenschuss et al. | 549/536 |
| 2014/0024846 A1 * | 1/2014 | Basrur et al. | 549/536 |

FOREIGN PATENT DOCUMENTS

| | | |
|---|---|---|
| DE | 4126285 | 2/1993 |
| EP | 0311712 | 4/1989 |
| EP | 2332650 | 6/2011 |
| WO | 2006/112493 | 10/2006 |

* cited by examiner

*Primary Examiner* — Maureen Wallenhorst
(74) *Attorney, Agent, or Firm* — Lois K. Ruszala; KSJLaw, LLC

(57) ABSTRACT

The present invention relates to methods for qualifying material for using in the cleaning of alkylene oxide equipment. Qualified material is not expected to contribute to the formation of determinable amounts of alkylene oxide by-products. Methods of cleaning alkylene oxide equipment, and alkylene oxide processes incorporating these methods are also provided.

12 Claims, No Drawings

METHOD OF QUALIFYING MATERIAL FOR USE IN CLEANING OF ALKYLENE OXIDE EQUIPMENT

FIELD

The present invention relates to methods for qualifying material for using in the cleaning of alkylene oxide equipment. Methods of cleaning alkylene oxide equipment, and alkylene oxide processes incorporating these methods are also provided.

BACKGROUND

Alkylene oxides are typically produced via the controlled oxidation of the desired alkylene in the presence of a plurality of supported catalysts. In order to maintain a commercially acceptable selectivity, the reaction temperature is desirably varies very little, e.g., for the production of ethylene oxide the optimum reaction temperature ranges from 225° C. to 250° C. At temperatures above 250° C., the selectivity of the reaction for ethylene oxide decreases rapidly with increasing temperature. Furthermore, the reactions involved in alkylene oxide production are exothermic, particularly, the side reaction to carbon dioxide. So, heat typically must be removed from the process so that the reactions can be properly controlled.

To facilitate heat removal, shell and tube reactors, i.e., comprising a large number of tubes of a small diameter within a shell, are typically used for such reactions. Even when these reactors are used, typically with a heat transfer medium supplied between the tubes and shell, the heat given off by the reaction is so high that high space velocities of the reactants must be maintained within the tubes. Although catalyst life can be extended to some degree by increasing the operating temperature, the amount of any such increase can be limited so that a decrease in selectivity is not realized. And so, before the process becomes economically unfeasible, the spent catalyst may typically be unloaded and the reactor tubes filled with new catalyst.

However, even though intended to invigorate the process, the unloading of old catalyst and reloading with new catalyst can introduce humidity or dew into the process. This dew can cause the internal surfaces of the reactor tubes and other components comprising carbon steel to rust. The presence of rust in the reactor tubes can result in greater numbers and/or amounts of impurities being formed during the alkylene oxide process. Such impurities can be difficult to separate from the desired end-product, and can result in a sub-optimal end-product being produced.

To address the formation of rust, many processes incorporate a cleaning step in their catalyst exchange process, in which an abrasive material may be used to clean the inner surfaces of the reactor tubes and/or other reactor components. It can be difficult to remove all of any such material so used, and so, such cleaning steps may inadvertently introduce impurities into the process.

It would thus be desirable to provide improved cleaning processes for alkylene oxide reactors and/or reaction components.

BRIEF DESCRIPTION

The present invention provides such processes. More particularly, the present invention relates to methods of qualifying abrasive blasting material for use in the cleaning of alkylene oxide reactors. Abrasive blasting material so qualified may be used in an improved cleaning process for alkylene oxide equipment, and the cleaning process incorporated into an alkylene oxide process, if desired.

In one aspect of the present invention then, there is provided a method for qualifying material for use in cleaning of alkylene oxide reactors. The method comprises determining a pre-contact amount of one or more alkylene oxide by-products in an alkylene oxide feed. In some embodiments, the alkylene oxide feed may comprise, e.g., substantially pure alkylene oxide, in which embodiments, the step of determining may comprise assuming the pre-contact amount to be negligible. The material and the alkylene oxide feed are caused to contact each other, and a post-contact amount of one or more alkylene oxide by-products in the feed determined after contact. The pre-contact amount is compared to the post-contact amount, and if the pre-contact amount is less than the post-contact amount, the material is disqualified for use in the cleaning of the alkylene oxide reactor. If, on the other hand, the pre--contact amount and post-contact amount are substantially the same, the material is acceptable for use in the cleaning process and is qualified for such use.

In another aspect, the present invention provides a method for cleaning alkylene oxide equipment. The method comprises qualifying a material for use in the cleaning method by determining a pre-contact amount of one or more alkylene oxide by-products in an alkylene oxide feed. The material and the alkylene oxide feed are caused to contact each other and a post-contact amount of one or more alkylene oxide by-products in the feed determined after contact. The pre-contact amount and the post-contact amount are compared, and if the pre-contact amount is greater than the post-contact amount, the material is qualified for use in the cleaning of the alkylene oxide equipment. The alkylene oxide is then cleaned with the qualified material, e.g., as by using the qualified material in a dry or wet abrasive blasting process.

Because the qualified material is not expected to contribute to the formation of alkylene oxide by-products if the material should come into contact with a feed utilized in the process, the cleaning method may advantageously be conducted during a catalyst changeout process. And so, in yet another aspect, a method for the production of an alkylene oxide is provided. The method comprises cleaning at least one piece of equipment utilized in the method with a qualified material. The material is qualified by determining a pre-contact amount of one or more alkylene oxide by-products in an alkylene oxide feed. The material and the alkylene oxide feed are caused to contact each other and a post-contact amount of one or more alkylene oxide by-products in the feed determined after contact. The pre-contact amount and the post-contact amount are compared, and if the pre-contact amount is greater than the post-contact amount, the material is qualified for use in the cleaning of the alkylene oxide equipment. The desired alkylene and oxygen are contacted in the presence of a catalyst under epoxidation conditions to produce the desired alkylene oxide, wherein a feed introduced into and/or generated by the alkylene oxide process contacts the cleaned equipment.

DETAILED DESCRIPTION

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

If ranges are disclosed, the endpoints of all ranges directed to the same component or property are inclusive and independently combinable (e.g., ranges of "up to 25 wt. %, or, more specifically, 5 wt. % to 25 wt. %," is inclusive of the endpoints and all intermediate values of the ranges of "5 wt. % to 25 wt. %," etc.). As used herein, percent (%) conversion is meant to indicate change in molar or mass flow of reactant in a reactor in ratio to the incoming reactant flow, while percent (%) selectivity means the change in molar flow rate of product in a reactor in ratio to the change of molar flow rate of a reactant.

Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described inventive features may be combined in any suitable manner in the various embodiments.

The present invention provides methods for qualifying material for use in the cleaning of alkylene oxide equipment. Methods of cleaning alkylene oxide equipment, e.g., such as reactors and other reaction components, using the qualified materials, and alkylene oxide processes incorporating these methods, are also provided.

More particularly, the qualification method comprises contacting a material to be qualified with an alkylene oxide feed. The amount(s) of one or more alkylene oxide by-products are determined in the feed before and/or after contact (pre-contact and post-contact amounts, respectively) with the material. Presence of these alkylene oxide by-products, at all, or in post-contact amounts greater than the pre-contact amounts, will result in the material not being qualified for use as a cleaner for the alkylene oxide equipment.

That is, in some embodiments, the alkylene oxide feed may be substantially pure and/or assumed to be substantially free of the by-product. In such embodiments, presence of any amount of the by-product post-contact with the material will indicate that the material participated in the formation of the by-product, and the material will not be qualified for use as a cleaner in the alkylene oxide reactor.

In other embodiments, a feed typical of one introduced into and/or generated by the process may be utilized and may comprise the by-product prior to contact with the material. In these embodiments, the concentration of the by-product in the feed will desirably be determined both pre- and post-contact with the material. The pre-contact and post-contact amounts will be compared. If the pre-contact amount is less than the post-contact amount, the material will not be qualified for use as a cleaner of the alkylene oxide equipment. If the pre-contact amount and the post-contact amounts are substantially the same, or within the standard range of deviation for the determination technique utilized, the material will be qualified for use as a cleaner of the alkylene oxide equipment.

Although the post-contact amount is not expected to be substantially less than the pre-contact amount, it is to be understood that if such a determination is made, the material will be qualified for use as a cleaner in the alkylene oxide equipment.

Any by-product of an alkylene oxide process may be determined, as contribution to the formation of any by-product may be an undesirable quality in a cleaning material. That is, since it can be difficult, or even impossible, to completely remove all cleaning material from alkylene oxide equipment, the material used in the cleaning process would desirably not substantially contribute to the formation of any by-product so that any inadvertent presence of the material after cleaning does not detrimentally impact the product quality and/or process capacity. Similarly, the concentration of any number of by-products may be determined, although increases in the concentration of one by-product in the feed after contact with the material may be sufficient to disqualify a material for use as a cleaner of the alkylene oxide equipment.

By-products that may be produced in alkylene oxide processes include aldehydes, dioxane, carbon monoxide and carbon dioxide. If aldehydes are produced, the particular aldehydes produced will depend upon the particular alkylene being used in the process. For many alkylenes, the formation of acetaldehyde is predominant, occurring upon isomerization of a portion of the alkylene oxide product, with lesser concentrations of acrolein, propionaldehyde and formaldehyde being formed.

Rust, or other carbonaceous or metallic deposits typically formed on alkylene oxide equipment surfaces may catalyze the isomerization of alkylene oxides to form aldehydes, which may explain these by-products' ubiquitousness. However, it has now been discovered that certain materials used in the cleaning of alkylene oxide equipment may do so as well. And so, the present methods have been developed to qualify the materials used in alkylene oxide equipment cleaning to ensure that they do not form reaction by-products, either via the aforementioned isomerization or otherwise, when contacted with feeds typical in such processes. And so, if materials qualified by the present methods are not completely removed from the alkylene oxide equipment after cleaning, materials qualified by the present method will yet not contribute to the formation of determinable quantities of the by-products.

Any material suitable for use as cleaner of alkylene oxide equipment may have the method described applied thereto. Typically, abrasives or grits may be used in the cleaning of alkylene oxide equipment, and many of these are known to those of ordinary skill in the art. Examples of such materials include but are not limited to, naturally occurring abrasives, such as e.g., calcite, emery, diamond dust, novaculite, pumice, rouge, sand, etc.; artificial or synthetically made abrasives such as boron nitride, ceramics, including ceramic aluminum oxide, alumina or aluminum oxide, glass powder, steel abrasive, silicon carbide, zirconia alumina; bonded or coated abrasives; glass beads; metal pellets and copper slag, among others. Any of these may be qualified using the disclosed methods.

The material to be qualified is desirably contacted with an alkylene oxide feed, i.e., a feed stream having a composition typical for alkylene oxide processes. Feed streams typical for such processes may comprise, for example, at least the alkylene desirably oxidized, a source of oxygen, one or more gas phase epoxidation promoters and the alkylene oxide desirably being produced. The alkylene oxide feed used to qualify the material may be any of these, or other components typical of epoxidation processes, used alone or in combinations of any number of them.

Many alkylenes are subjected to such processes, and examples of those that may desirably be oxidized include, but are not limited to, 1,9-decadiene, 1,3-butadiene, 2-butene, isobutene, 1-butene, propylene, ethylene, or combinations of these. In some embodiments, the alkylene comprises ethylene or propylene, and may desirably comprise ethylene.

Furthermore, oxygen may be supplied to epoxidation processes in the form of any oxygen-containing stream, such as air, or as pure oxygen, or as oxygen-enriched air.

The resulting alkylene oxide will depend upon the alkylene introduced into the process, and in some embodiments may desirably comprise ethylene oxide or propylene oxide, and in some embodiments may more desirably comprise ethylene oxide.

Typically, gas phase promoters useful in epoxidation reactions include organic compounds, and in particular include organic halides, e.g., bromides or chlorides. Even more particular examples of chlorohydrocarbons that may be present in the alkylene oxide feeds include, but are not limited to, methyl chloride, ethyl chloride, ethylene dichloride, vinyl chloride, or any combination of these. Many alkylene oxide processes utilize ethyl chloride and ethylene dichloride as gas phase promoters and these, in particular, may be present in the alkylene oxide feed utilized in the method.

Any gas phase promoter(s) initially present in the feed may typically react upon contact with the catalyst and under epoxidation reaction conditions and so, the alkylene oxide feed utilized may include not only the introduced promoter(s), but any or all of its/their reaction products that may be formed during application of the method.

In those embodiments wherein the material to be tested is contacted with a feed comprising the desired alkylene oxide, a substantially pure alkylene oxide gas may not be expected to comprise any amount of by-product. And so, rather than measuring this expectedly negligible quantity, the pre-contact amount of by-product in the feed may be assumed to be zero, and the determination step may comprise making this assumption. In such embodiments, the presence of any amount of by-products after contact with the material would be considered indicative that the material had contributed to the formation of the same, and the material would not be qualified for use in the cleaning of the alkylene oxide equipment.

A feed introduced into and/or produced by an alkylene oxide process may also be used, in which case the feed may be expected to comprise an amount of one or more by-products, and so, a pre-contact amount of the one or more by-products, i.e., the amount of by-products present in the feed prior to contact of the feed and the material, may desirably be determined prior to contacting the feed and the material.

The material to be qualified may be contacted with the desired feed at any desired conditions. In some embodiments, it may be desirable for the contact to occur at conditions typical for steady-state operation of an alkylene oxide process. Typical operating conditions for an alkylene oxide process include introducing a feed stream containing alkylene (e.g., ethylene) and oxygen or an oxygen-containing gas and a gas phase promoter at parts per million level to a catalyst-containing reactor at a temperature of from 200° C. to 300° C. at steady state operating conditions, and a pressure which may vary between 5 atmospheres (506.5 kPa), at steady-state operating conditions, depending upon the mass velocity and productivity desired.

However, given that the material to be qualified may be introduced into an alkylene oxide reactor at a catalyst change, contact may also desirably occur at conditions typical for start-up of an alkylene oxide process. In some embodiments then, contact between the material and the alkylene oxide feed may occur at a temperature of from ambient temperature to 300° C., and a pressure which may vary between ambient and 30 atmospheres (3039.5 kPa).

The material and the desired alkylene oxide feed may be caused to contact each other in any way that allows at least a portion of the alkylene oxide feed to contact at least a portion of the material. The material may be supported or unsupported within a vessel or tube, and the alkylene oxide feed caused to flow around, over or through the material, with or without agitation or stirring, so long as some amount of the feed comes into contact with some portion of the material.

The pre-contact and post-contact amounts of by-product may be determined using any suitable method, among the many such methods known to those of ordinary skill in the art of analytical chemistry. The particular test method used will depend upon what by-product is being tested for, and is readily determined by those of ordinary skill in the art. The determinations may be either qualitative, e.g., in those embodiments wherein the alkylene oxide feed caused to contact the material is believed or known to be substantially free of the by-product(s), or quantitative, e.g., in those embodiments wherein the alkylene oxide feed is believed or known to contain a determinable quantity of the by-product(s).

Quantitative methods suitable may include methods based upon a change in color, mass, volume or density attributable to the presence of the by-products but not indicative of mass or concentration. Qualitative tests, on the other hand, may be used when the determination of a mass or concentration is desired or required, and any of these may be used to determine the pre-contact and post-contact amounts. Many qualitative tests are known to those of ordinary skill in the art, and include, e.g., spectroscopic methods, including UV-Vis spectroscopy, Raman spectroscopy, infrared spectroscopy, NMR spectroscopy; mass spectrometry; electrochemical analysis, or thermal analysis. Any of these may be preceded by a separation process, e.g., chromatography or electrophoresis, if desired or required, in order to enhance the ease or accuracy of the determination. Similarly, the chosen methods may be carried out in-line i.e. the sample to be tested may be obtained by taking a side stream from an operating process or test. Whatever the chosen separation and/or determination method, it/they will be capable of being carried out using information known and/or readily available by/to those of ordinary skill in the art.

The pre-contact, either as assumed or determined, and post-contact amounts will be compared. If the pre-contact amount is less than the post-contact amount, the material will not be qualified for use as a cleaner of the alkylene oxide equipment. If the pre-contact amount and the post-contact amounts are substantially the same, or within the standard range of deviation for the determination technique utilized, the material will be qualified for use as a cleaner of the alkylene oxide equipment. As mentioned above, although the post-contact amount is not expected to be substantially less than the pre-contact amount, it is to be understood that if such a determination is made, the material will be qualified for use as a cleaner in the alkylene oxide equipment.

Since a material qualified according to the method does not produce substantial amounts of by-products when contacted with an alkylene oxide feed, it can be used in a method of cleaning alkylene oxide equipment, and even if residual amounts of the qualified material are left behind in the cleaned equipment, product quality and production capacity will not be detrimentally impacted. And so, also provided herein is a method for cleaning alkylene oxide equipment.

The method involves qualifying a material for use in the cleaning process as disclosed. Once qualified, the material may be utilized to clean the equipment, e.g., as with a conventional abrasive blasting procedure. As is well known in the art, in abrasive blasting procedures, a stream of abrasive material is forcibly propelled against a surface under high pressure and/or at high velocity. Such procedures may be carried out using any number of commercially available mobile dry or wet abrasive blast systems or blast cabinets.

Since a material qualified as disclosed herein is not expected to contribute to the formation of by-products in an alkylene oxide process, the methods disclosed herein may advantageously be employed during such a process.

That is, during many alkylene oxide processes, the catalyst may desirably be changed one or more times, when/if the productivity and/or capacity of the process declines to a sub-optimal level. A typical exchange process involves unloading the catalyst, and then cleaning the reactor tubes to remove any rust or carbonaceous deposits on the walls of the tubes and then purging the tubes with dry nitrogen or dry air. The reactor is then reloaded with catalyst, and the alkylene oxide process resumed. The use of a material qualified according to the disclosed method for the cleaning is expected to result in increased efficiency of the process after cleaning, as compared to cleaning processes employing unqualified or unqualifiable materials. This is because even if some qualified material is inadvertently left in the equipment and subsequently comes into contact with an alkylene oxide feed, the qualified material is not expected to contribute to the formation of by-products, whereas the unqualified or unqualifiable material would be expected to contribute to the formation of by-products.

Some embodiments of the invention will now be described in detail in the following examples.

EXAMPLE 1

A 0.959 inch (2.4 cm) inside diameter jacketed vertical reactor tube is charged with 24.5 feet (7.47 m) of 8 mm silver-based alumina ethylene oxide catalyst. Hot oil circulating through the jacket controlled reactor temperature. Process gas flow is in the upward direction (concurrent with respect to oil flow). The catalyst bed is kept from fluidizing by depositing an aluminum hold-down bar on top of it. A cylindrical basket, smaller in diameter than the tube ID, containing 25 grams of Scangrit HD blasting sand is set on top of the hold down bar. The reactor is operated at the following approximate inlet conditions: 240 psig (1656 kPa gauge), 481 scfh (3900 hr$^{-1}$ gas hourly space velocity), 8.5% $O_2$, 5.5% $CO_2$, 28% $C_2H_4$, 0.1% $C_2H_6$, 2.1 ppm chloroethane, and the balance being $N_2$ (all concentrations are mole percent or mole parts per million). Oil temperature was controlled to produce approximately 2.9% ethylene oxide in the reactor outlet gas.

A sample of the product gas (ethylene oxide feed) at the reactor outlet after the hold down bar was sent through a sampling line to an on-line analyzer (Gas Chrornatograph), where the reactor outlet gas composition and the by-product acetaldehyde concentration were determined.

The following Table 1 summarized the results before and after the basket was inserted in the reactor outlet:

| Outlet conditions | No Sand or Basket | Basket with Scangrit HD |
|---|---|---|
| Gas temperature, ° C. | 244.9 | 244.2 |
| % EO | 2.89 | 2.97 |
| % $O_2$ | 4.85 | 4.90 |
| % $CO_2$ | 7.19 | 8.02 |
| % $C_2H_4$ | 24.82 | 25.59 |
| Psig/kPa gauge | 235/1621.5 | 235/1621.5 |
| Ppm acetaldehyde | 2.27 | 2.23 |

These results show that, at similar operating conditions, the acetaldehyde concentration is no higher with the sand sample present than in its absence. According to the present method, it can be concluded that Scangrit HD is acceptable for use as an abrasive cleaner on ethylene oxide reaction equipment.

EXAMPLE 2

A 0.959 inch (2.4 cm) inside diameter jacketed vertical reactor tube is charged with 25 feet (7.62 m) of 8 mm silver-based alumina ethylene oxide catalyst. Hot oil circulating through the jacket controlled reactor temperature. Process gas flow is in the upward direction (concurrent with respect to oil flow). The catalyst bed is kept from fluidizing by depositing an aluminum hold-down bar on top of it. A cylindrical basket, smaller in diameter than the tube ID, containing 26 grams of DuPont Starblast blasting sand is deposited in the outlet end of the reactor. The reactor is operated at the following approximate outlet conditions: 235 psig (1621.5 kPa gauge), 275° C., 800 scfh (6400 hr$^{-1}$ gas hourly space velocity), 6.0% $O_2$, 8.6% $CO_2$, 3.0% $C_2H_4$, 0.1% $C_2H_6$, 1.3% ethylene oxide, 4 ppm chloroethane, and the balance being $N_2$ (all concentrations are mole percent or mole parts per million).

With the Starblast sand present, outlet acetaldehyde concentration is 8.9 ppm. Without the Starblast sand, outlet acetaldehyde concentration is 4.8 ppm. According to the present method, it is possible to conclude that DuPont Starblast sand is not acceptable for use as an abrasive cleaner on ethylene oxide reaction equipment.

The invention claimed is:

1. A method for qualifying a material for use in cleaning of alkylene oxide equipment, comprising:
    Determining a pre-contact amount of one or more alkylene oxide by-products in an alkylene oxide feed;
    Causing the material and the alkylene oxide feed to contact each other;
    Determining a post-contact amount of one or more alkylene oxide by-products in the feed after contact; and
    Comparing the pre-contact amount to the post-contact amount, and if the pre-contact amount is greater than or equal to the post-contact amount, qualifying the material for use in the cleaning of the alkylene oxide equipment.

2. The method of claim 1, wherein the alkylene oxide feed comprises substantially pure alkylene oxide, and the step of determining the pre-contact amount comprises assuming the pre-contact amount of the one or more alkylene oxide by-products to be substantially zero.

3. The method of claim 2, wherein if the post-contact amount is greater than zero, the material is disqualified for use in the cleaning of alkylene oxide equipment.

4. The method of claim 3, wherein the step of determining the post-contact amount comprises conducting a qualitative measurement.

5. The method of claim 1, wherein the alkylene oxide feed comprises a feed introduced into and/or generated by an alkylene oxide process and wherein the step of determining the pre-contact amount comprises conducting a quantitative measurement of one or more alkylene oxide by-products in the feed prior to contact with the material.

6. The method of claim 1, wherein the alkylene oxide feed comprises a feed introduced into and/or generated by an alkylene oxide process and wherein the step of determining the post-contact amount comprises conducting a quantitative measurement of one or more alkylene oxide by-products in the feed after contact with the material.

7. The method of claim 1, wherein the one or more alkylene oxide by-product(s) comprise carbon monoxide, carbon dioxide, dioxane, one or more aldehydes, or combinations of these.

8. A method for cleaning alkylene oxide equipment, comprising:
   Qualifying a material for use in the cleaning method by:
      Determining a pre-contact amount of one or more alkylene oxide by-products in an alkylene oxide feed;
      Causing the material and the alkylene oxide feed to contact each other;
      Determining a post-contact amount of one or more alkylene oxide by-products in the feed after contact; and
      Comparing the pre-contact amount to the post-contact amount, and if the pre-contact amount is greater than or the same as the post-contact amount, qualifying the material for use in the cleaning of the alkylene oxide equipment;
   Using the qualified material to clean the alkylene oxide equipment.

9. The method of claim 8, wherein the qualified material is utilized in an abrasive blasting method to clean the alkylene oxide equipment.

10. A method for the production of an alkylene oxide, comprising:
    Using a qualified material to clean at least one piece of equipment used in the method, wherein the material is qualified by:
       Determining a pre-contact amount of one or more alkylene oxide by-products in an alkylene oxide feed;
       Causing the material and the alkylene oxide feed to contact each other;
       Determining a post-contact amount of one or more alkylene oxide by-products in the feed after contact; and
       Comparing the pre-contact amount to the post-contact amount, and if the pre-contact amount is greater than or equal to the post-contact amount, qualifying the material for use in the cleaning of the alkylene oxide equipment;
    contacting an alkylene and oxygen in the presence of a catalyst under epoxidation conditions in the cleaned equipment to produce an alkylene oxide, wherein a feed introduced into and/or generated by the alkylene oxide production process contacts the cleaned equipment.

11. The method of claim 10, wherein the alkylene oxide equipment comprises an alkylene oxide reactor and the cleaning is conducted during a catalyst changeout.

12. The method of claim 10, wherein the alkylene oxide comprises ethylene oxide or propylene oxide.

\* \* \* \* \*